United States Patent [19]

Lonardo

[11] Patent Number: 5,298,013
[45] Date of Patent: * Mar. 29, 1994

[54] METHOD OF HEALING THE DECABITUS ON THE HEEL OF A BEDFAST PATIENT

[75] Inventor: Robert Lonardo, Treasure Island, Fla.

[73] Assignee: Restorative Care of America Incorporated, Clearwater, Fla.

[*] Notice: The portion of the term of this patent subsequent to Dec. 14, 2010 has been disclaimed.

[21] Appl. No.: 52,517

[22] Filed: Apr. 29, 1993

Related U.S. Application Data

[60] Division of Ser. No. 20,222, Feb. 16, 1993, Pat. No. 5,269,748, which is a continuation of Ser. No. 399,365, Sep. 21, 1973, abandoned, which is a continuation-in-part of Ser. No. 237,643, Mar. 24, 1972, abandoned, which is a continuation-in-part of Ser. No. 86,647, Nov. 4, 1970, abandoned.

[51] Int. Cl.$^5$ .............................................. A61F 5/00
[52] U.S. Cl. ..................................... 602/28; 602/27; 128/882
[58] Field of Search ........................ 602/5, 23, 27–29; 128/845, 882

[56] References Cited

U.S. PATENT DOCUMENTS

| Re. 27,957 | 4/1974 | Larson . | |
|---|---|---|---|
| 114,669 | 5/1871 | Grant . | |
| 433,227 | 7/1890 | Beacock . | |
| 735,860 | 8/1903 | Darby | 602/29 |
| 839,223 | 12/1906 | Stevens | 602/27 |
| 1,334,596 | 3/1920 | Crouch . | |
| 1,656,322 | 1/1928 | Fischer . | |
| 1,769,681 | 7/1930 | Ettinger | 602/23 |
| 1,948,534 | 2/1934 | Nelson et al. . | |
| 2,492,920 | 12/1949 | Koster . | |
| 3,086,522 | 4/1963 | Frohmader . | |
| 3,171,407 | 3/1965 | Rogus . | |
| 3,304,937 | 2/1967 | Callender, Jr. . | |
| 3,345,654 | 10/1967 | Noble . | |
| 3,523,526 | 8/1970 | Phelps . | |
| 3,557,782 | 1/1971 | Wafer . | |
| 3,584,622 | 6/1971 | Domenico . | |
| 3,589,359 | 6/1971 | Hill . | |
| 3,606,884 | 9/1971 | Peter . | |
| 3,618,946 | 11/1971 | Lee . | |
| 3,779,654 | 12/1973 | Horne . | |

FOREIGN PATENT DOCUMENTS

346649 of 1960 Switzerland .

Primary Examiner—Richard J. Apley
Assistant Examiner—Linda C. M. Dvorak
Attorney, Agent, or Firm—Zarley, McKee, Thomte, Voorhees & Sease

[57] ABSTRACT

A therapeutic leg and foot device comprising an L-shaped member having an elongated channel-like portion adapted to fit the posterior region of the lower leg and a foot portion extending integrally at right angles therefrom. The integral connection is curved to avoid contact with the patient's heel when the device is in place. The channel shape flattens out at the curved portion and is narrowed to promote the required flexing at this point. The device is constructed of resilient transparent acrylic plastic material which is resilient under a stress load but has sufficient rigidity to maintain a bed patient's foot in properly disposed position to prevent bed sores or drop foot. However, when used in the correction of drop foot, the foot portion is flexed away from the perpendicular to an obtuse angle with the leg portion to conform to the deformity. In this position, the device exerts a 30 to 50 lb. pressure on the foot area to bias the foot back into normal position. There is also an equal amount of pressure or counter force on the lateral arch to correct outward turning of a foot usually associated with a foot drop deformity. This rigid flexibility also permits its use as an ambulation aid in gait training. The device is provided with releasable means for securing to the patient's foot. Attachments may be made for preventing undesirable rotation of the leg; for making the device rigid to maintain the immobility of the foot and heel; and for maintaining the bed sheets and blankets in spaced relation to the patient's toes.

6 Claims, 2 Drawing Sheets

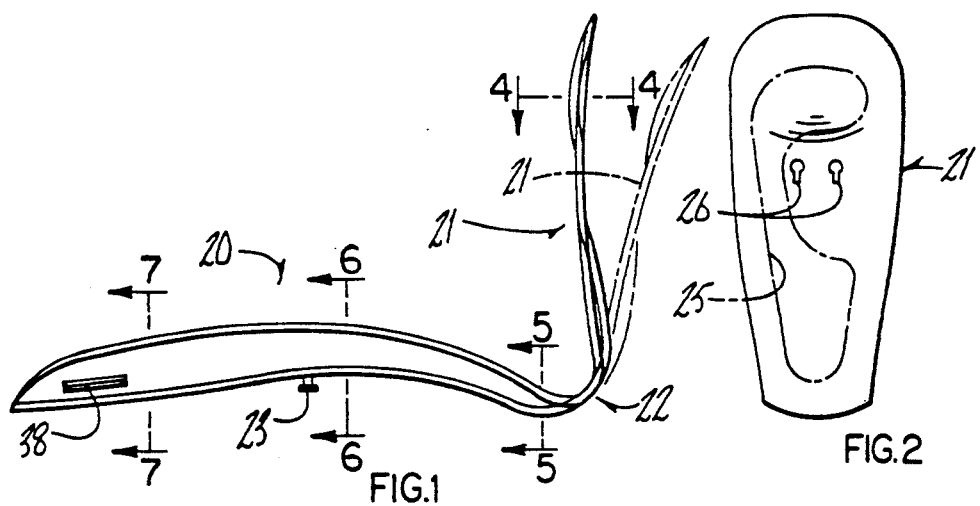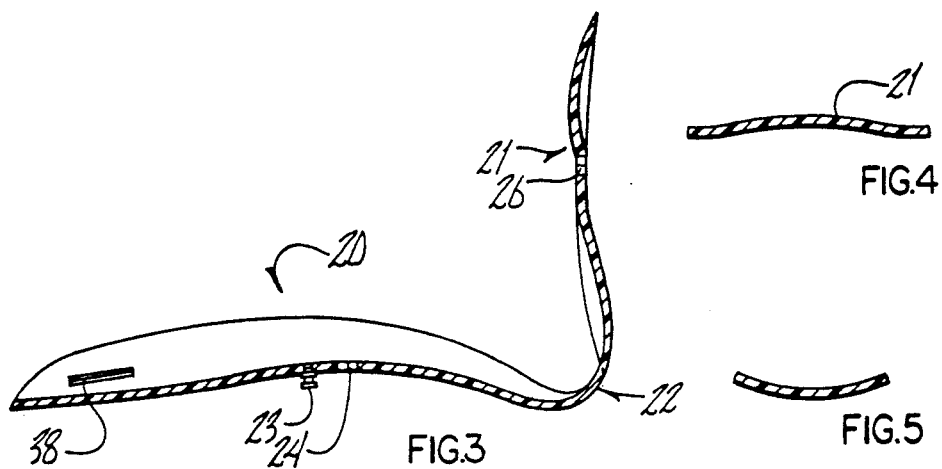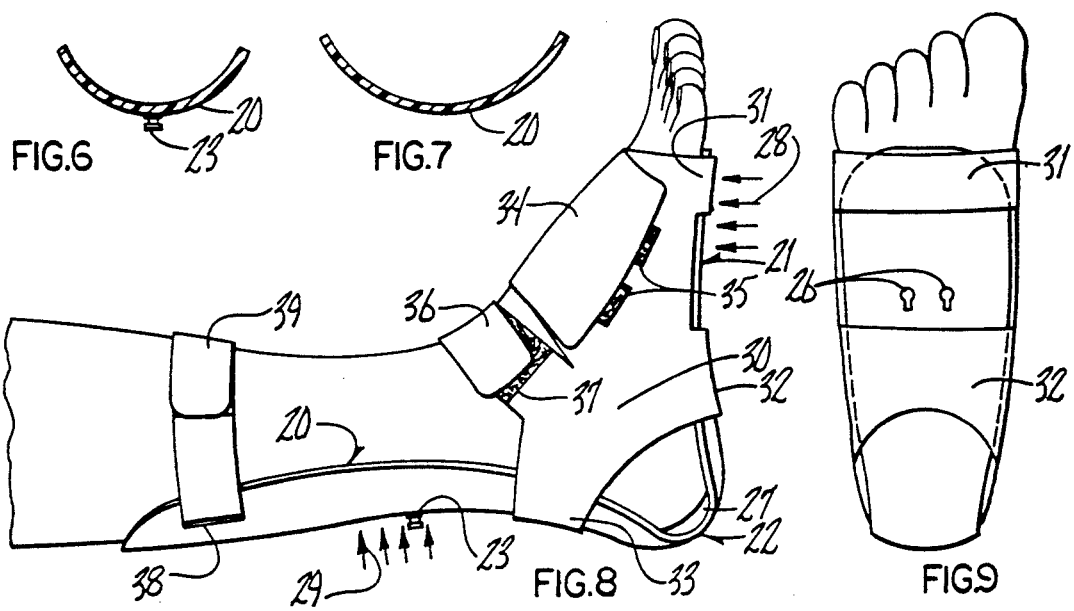

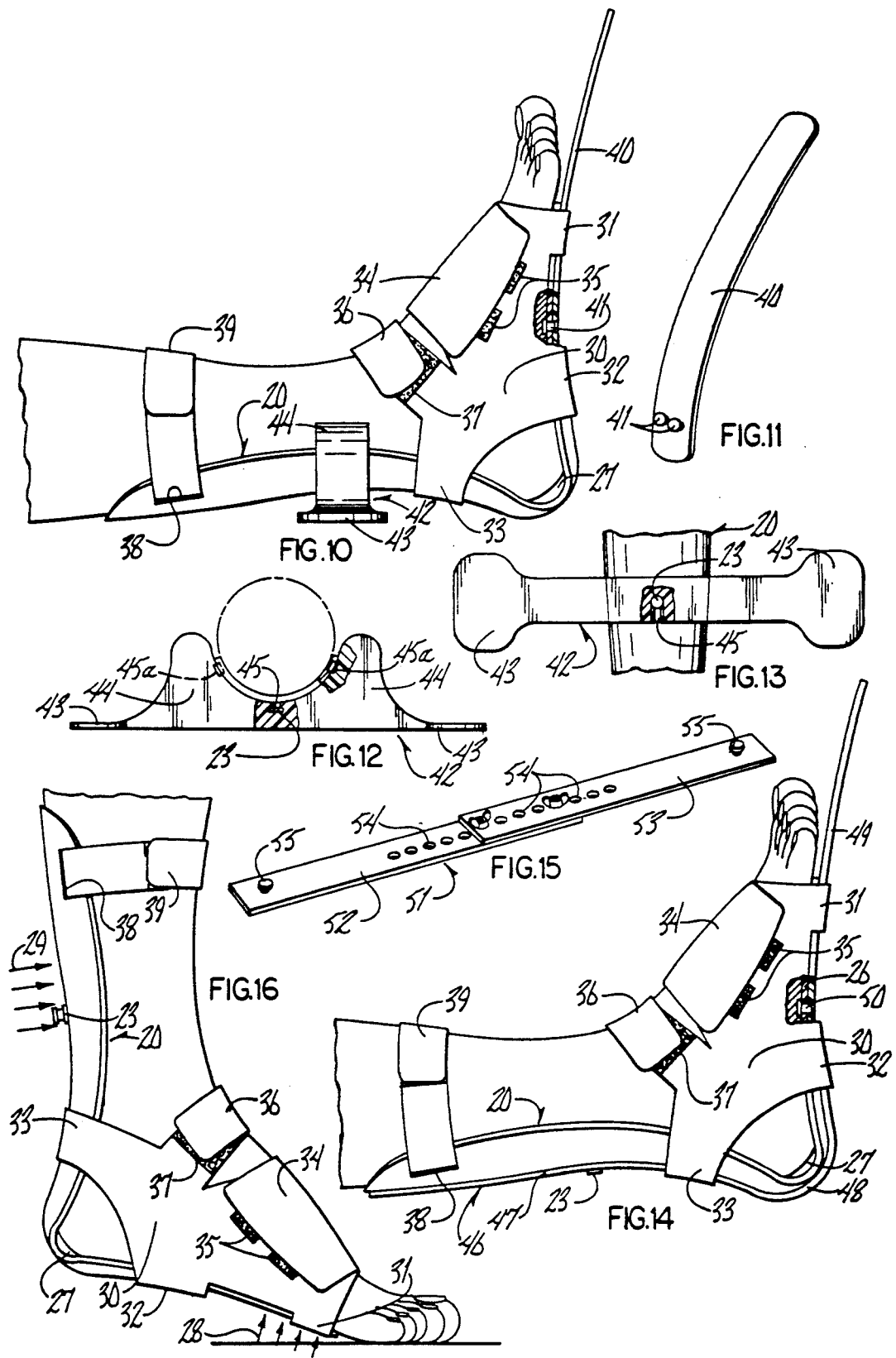

METHOD OF HEALING THE DECABITUS ON THE HEEL OF A BEDFAST PATIENT

This application is a division of Ser. No. 08/020,222 filed on Feb. 16, 1993, now U.S. Pat. No. 5,269,748, which is a File Wrapper Continuation of copending application Ser. No. 05/399,365 filed Sep. 21, 1973, now abandoned, which was a continuation-in-part, all under the same title, of co-pending application Ser. No. 237,643 filed Mar. 24, 1972, now abandoned, which was a continuation-in-part of application Ser. No. 86,647 filed Nov. 4, 1970, now abandoned.

BACKGROUND OF THE INVENTION

Therapeutic devices for preventing drop foot, maintaining the patient's foot in proper position, and for acting as a heel guard are well known in the art. For example, U.S. Pat. No. 3,345,654 illustrates a typical construction of such a device.

However, these devices are merely splints and are not primarily designed to correct an existing condition. They are not designed to apply a corrective pressure to the foot. As a matter of fact, their rigidity precludes their use to correct an existing condition.

Furthermore, they are not designed to act as a walking brace or ambulation aid in gait training. This is important where the patient has been bed ridden for an extended period. This is especially true where the foot and leg have been held rigid.

SUMMARY OF THE INVENTION

The device of the present invention is a truly therapeutic device and not a mere leg brace or splint. It is designed to provide a steady and accurately placed pressure on the sole and calf to correct existing deformities of the foot. Provision is made for augmenting the pressure, if necessary. When in place, the device can be worn inside of the shoe and act as an ambulation aid. This it does by applying an active corrective pressure under normal walking conditions and flexing with the movement of the toes and heel as in natural walking. All this while the pressure is applied to the first, third, fourth and fifth metatarsal bones and arch, to bring the foot automatically upward.

The device is also highly versatile. It can be made rigid by the addition of an easily mounted attachment for the purpose of holding the foot or heel in a rigid position. Another attachment will prevent rotation of the patient's foot, leg or hip. This may be necessary in a post operative condition.

A further attachment keeps sheets and blankets away from the patient's toes and foot while lying in bed. And finally the device is made to receive any other suitable attachment such as a spreader for retaining the legs in spread position.

It should be noted that in the case of medical or surgical work on the heel and adjacent areas, the device will retain the foot in fixed position while maintaining a spaced relation with the heel. This permits light bandaging, makes it easily accessible to the doctor for examination, and eliminates the need for immobilizing heavy bandages or casts.

DESCRIPTION OF THE DRAWINGS

FIG. 1 is a side elevation of the device of the present invention showing its flexing position and dynamic return;

FIG. 2 is a longitudinal section thereof;

FIG. 3 is an end view showing the area for the proper application of corrective pressure;

FIG. 4 is a section taken on line 4—4 on FIG. 1;

FIG. 5 is a section taken on line 5—5 on FIG. 1;

FIG. 6 is a section taken on line 6—6 on FIG. 1;

FIG. 7 is a section taken on line 7—7 on FIG. 1;

FIG. 8 is a view similar to FIG. 1 with the device mounted on a patient in prone position;

FIG. 9 is an end view similar to FIG. 3 with the device mounted as shown in FIG. 8;

FIG. 10 is a view similar to FIG. 8 showing the mounting of several attachments;

FIG. 11 is a perspective view of the attachment for maintaining the bed sheet and blanket spaced from the toes;

FIG. 12 is a front view of the attachment for preventing rotation;

FIG. 13 is a bottom view of the attachment shown in FIG. 12, partially broken away;

FIG. 14 is a view similar to FIGS. 8 and 10 showing the addition of still another attachment;

FIG. 15 is a perspective view of the spreading attachment; and

FIG. 16 is a side elevation illustrating the use of the device as an ambulation aid in an existing contracture deformity.

DESCRIPTION OF THE INVENTION

Referring to the drawings in more detail, the device of the present invention is more clearly illustrated in FIGS. 1 to 7, inclusive. The device is molded of an acrylic transparent thermo-plastic material in a general L-shape, forming a leg portion 20 and a foot portion 21 extending integrally from a curved heel section 22 at right angles to the leg portion 20.

The leg portion 20 is contoured and channeled, as shown in FIGS. 1, 3, 6 and 7, so as to comfortably receive the posterior region of the lower leg. It is specifically depressed just above the ankle bone, see FIG. 8, and below the greater calf to act as a support and receive most of the weight concentration. This is the area that supplies the counter-force for the flexing pressure of the foot portion 21 as hereinafter described. The portion 20 is provided at this point with a central stud 23 and a pair of spaced keyhole slots 24 adjacent the stud 23 toward the heel end.

The foot portion 21 is also contoured and channeled but to a lesser degree, see FIGS. 1, 2 and 4. The length of the portion 21 is such that its upper end terminates well short of the patient's toes when worn as in FIGS. 8 and 9. The device is flexible, and when the foot portion 21 is pulled into the dotted line position shown in FIG. 1, it will apply pressure to the bottom of the heel, the lateral arch, and the transverse metatarsal bones and arch as shown in the broken line area 25 in FIG. 2. The central portion of the foot portion 21 is also provided with a pair of keyhole slots 26, see FIGS. 2 and 9.

To permit a proper flexing action, the heel portion 22 is provided with an area of the least amount of contouring and channeling, being almost flat, see FIGS. 3 and 5. The curvature is such that not only is there no pressure applied to the rear of the patient's heel, but there is an actual space 27 between the patient's heel and the heel portion 22 when the device is in place as in FIGS. 8 and 9.

Since the most important function of the device is its ability to flex at 22 to apply the proper therapeutic pressure, the material and construction at this point is of prime importance. First of all, rigidity along the portion 20 is supplied in part by its channel shape. This channeling gradually disappears as the heel portion 22 is reached. FIG. 7 shows the largest and deepest channeling, FIG. 6 is smaller, and FIG. 5, closest to the portion 22, shows it virtually gone. At the point 22, the device should be substantially (possibly not completely) flat. Furthermore, as can be seen in FIGS. 5, 6 and 7, the device is narrowest at this point. The degree of flexibility can thus be controlled by the degree of channeling and the narrowing of the material at the heel.

Since flexibility is essential, the material is also important. The device is made of an acrylic thermo-plastic material approximately 0.125" in thickness. In small sizes for children, it may be only 0.087" thick. The leg portion 20 is approximately 10" long and the foot portion 21 is approximately 6" long. The heel portion 22 is approximately 1½" across. To complete the construction, the leg portion 20 is approximately 4" at its maximum width, the foot portion 21 3¾", and the heel portion 22 only 2" wide.

With the above construction, the device will apply a pressure of 30 to 50 lbs. when flexed. Applicant has found that the acrylic plastic has the required characteristics. However, the constant flexing and use under stress loads requires fatigue strength, longevity, and resiliency under the stress loads over long periods of time. The acrylic filling these requirements is called "Nyloplex" and is sold by Fillauer Surgical Supplies of Chattanooga, Tennessee. A product called "Lexan" manufactured by General Electric Company is also satisfactory but slightly more sluggish in its flexing reaction. As with most acrylics, the above products have a "memory" so that they return to their original right angled form after each flexing.

The device is light in weight, approximately 6 oz., but the flexible acrylic has a tensile strength to withstand up to 250 lbs. of continuous resistance without fracturing, losing shape, or distorting. When flexed into the dotted line position shown in FIG. 1, it will exert a force of 30 to 50 lbs. pressure to the area shown by the arrows 28 in FIG. 8. This pressure is applied against the counter-pressure at the calf shown by the arrows 29.

This is the action necessary to correct a foot deformity such as drop foot. The patient's foot is placed into the device by flexing the foot portion 21 to an angle, FIG. 1, which will permit the insertion of the foot, then the portion 21 is released to apply the pressure. Any suitable means may be used to secure the device to the leg and foot of the patient. For example, viewing FIGS. 8 and 9, I use a soft leather sleeve or sandal 30 which is slipped over the patient's foot and the foot portion 21 of the device. It is provided with a cut out heel portion with strips 31 and 32 passing under the foot and strips 33 behind the upper heel. The front is provided with a flap 34 having any suitable fastening means such as the Velcro fastener 35, for securement around the instep. An additional strip 36, provided with a Velcro fastener 37, extends above the ankle region. In addition to the sandal 30, the leg portion 20 is provided with slots 38 adjacent the rear upper end. A strip 39 extends around the leg through the slots 38 to complete the mounting of the device.

With the device worn as shown in FIGS. 8 and 9, the application of the pressure as illustrated by the flexing action in FIG. 1 and the arrows 28 in FIG. 8 will correct any drop foot or similar deformity and will certainly prevent the formation thereof. Furthermore, the counter force pressure on the lateral arch will correct any outward turning of the foot usually associated with a foot drop deformity. The device is comfortable and will be tolerated by the patient over extended periods of time. It eliminates the need for weighted bags, foot boards, pillows, heavy dressings, and many other ineffective methods of treatment. Note that the device is always in place, whereas the other methods are hit or miss depending on the position of the patient. The device will accommodate either the right or left foot, male or female, and may be reused on another patient.

The device is also designed to be used in the prevention of heel decubitus and aid in the healing of an existing one. Since the heel is suspended at 27 it clears the tender area and there is no contact or pressure. The transparency of the device allows the involved area to be constantly observed. In surgery, the device holds the foot rigid and allows the use of a light bandage for frequent observation by the doctor during healing.

When the device is in use, it may also be found necessary to keep the sheets and blankets off the patient's toes. To this end I provide the attachment shown in FIGS. 10 and 11. An elongated strap-like member 40 is curved to conform to the contour of the foot portion 21. It is provided with a pair of studs 41 adjacent the lower end. The member 40 is slipped under the strip portion 31 of the member 30, the studs 41 locking in the slots 26. The member 40 thus extends above the toes and keeps the sheets and blankets at a distance.

It is often desirable to provide means for preventing rotation of the patient's leg for hip or leg conditions and for providing immobility after operations in these areas. This is accomplished by the attachment shown in FIGS. 10, 12 and 13. An elongated plastic member 42 is provided with a flat bottom and enlarged ends 43. The center is provided with a cradle portion 44 adapted to receive the leg and leg portion 20 (broken lines in FIG. 12). The leg portion 20 is locked to the member 42 by providing the cradle portion 44 with a central keyhole slot 45 for receiving the stud 23. For additional immobility, the parts may be provided at each side with snap fasteners 45a on the cradle portion 44 and leg portion 20. As can be seen in FIGS. 10 and 12, the attachment 42 prevents rotation of the patient's leg in the device. Note that this attachment can be used simultaneously with the attachment 40 as shown in FIG. 10.

While the construction is designed to provide a flexing pressure of 30 to 50 lbs., in certain extreme conditions it may be desirable to increase the pressure by an additional 20 to 25 lbs. In such cases the attachment shown in FIG. 14 may be used. This comprises an L-shaped strip 46 of the same flexible acrylic material as the device itself. It is shaped to the outer contour of the device, having a leg portion 47, heel 48, and a foot portion 49. The foot portion 49 extends upwardly beyond the toes to perform the function of the attachment 40 to space the sheets and blankets from the toes. The strip 46 is provided with a keyhole slot for receiving the stud 23 of the leg portion 20 and is provided with studs 50 for attachment to the keyhole slots 26 in the foot portion 21. In the mounted position shown in FIG. 14, the strip 46 adds 20 to 25 lbs. to the flexed pressure of the foot portion 21.

In certain surgical applications it may become necessary to retain the foot in a rigid, immovable position such as shown in FIG. 14. In such cases, the attachment 46 is made of a rigid material such as a metal or rigid plastic without flexibility. Its construction and method of mounting would be the same as the member 46, but it would hold the foot rigidly by counteracting the flexibility of the main device.

Another useful attachment for the device is the spreader 51 shown in FIG. 15. In surgical procedures involving thighs, groin and related areas, it may be necessary to keep the patient's legs spread during healing. In such cases a device of the present invention is first mounted on each foot and leg. The spreader 51 comprises a pair of strips 52 and 53 adjustably connected at 54. At their outer ends, the strips 52 and 53 are provided with studs 55 which can be mounted in the keyhole slots 24 on the leg portions 20 to spread the legs apart. Alternatively, the spreader 51 can be mounted on the foot sections 21 by attaching the studs 55 to the keyhole slots 26. Either method will result in the same spread position.

As stated hereinabove, one of the advantages of the present invention is its use as an ambulation aid in gait training. As can be seen in FIG. 16, the application of pressures at the points 28 and 29 is of prime importance when walking. Thus the inherent flexibility of the device will tend to force the foot into a proper walking action including the flexing of the foot and lifting to move into forward position. The device will apply the same pressure action while walking as it does to correct an abnormality in the prone position shown in FIG. 8. It should be noted that the fact that the foot section 21 is short of the toes permits natural movement of the toes and feet while walking. This also permits the patient's own shoe to be worn directly over the device without discomfort. The device thus acts as a walking brace and the pressure on the foot at 28 ensures a proper walking step without dragging, regardless of the corrections being made to the foot position.

The present invention therefore provides a therapeutic leg and foot device of simple construction and designed for its intended purpose. However, the device is extremely versatile in use. It can be used in a prone or in an ambulating position, and it can be used with its attachments to alleviate, correct, or prevent various conditions.

Other advantages of the present invention will be readily apparent to a person skilled in the art.

I claim:

1. The method of healing or preventing decubitus on the heel of a bedfast patient, comprising,
   placing on the leg and foot of said patient an L-shaped member having a leg portion, a heel portion on one end of said leg portion, and a foot portion extending from said heel portion at right angles to said leg portion,
   forming the shape of said heel portion so that the shape alone of said heel portion will provide a space between the patient's heel and said heel portion to prevent the application of pressure to the patient's heel by said heel portion when the lower leg and the sole of the foot of said patient are in intimate contact with said leg portion and said foot portion, respective,
   and securing said L-shaped member to the leg and foot of said patient by using a sandal extending substantially over said foot portion and the foot of the patient, and cutting out a heel portion of said sandal adjacent said heel portion of said L-shaped member and said space.

2. The method of claim 1 wherein said L-shaped member is formed so that said leg, heel and foot portions are integral with each other.

3. The method of healing or preventing decubitus on the heel of a bedfast patient, comprising,
   placing on the leg and foot of said patient an L-shaped member having a leg portion, a heel portion on one end of said leg portion, and a foot portion extending from said heel portion at right angles to said leg portion,
   forming the shape of said heel portion so that the shape alone of said heel portion will provide a space between the patient's heel and said heel portion to prevent the application of pressure to the patient's heel by said heel portion when the lower leg and the sole of the foot of said patient are in intimate contact with said leg portion and said foot portion, respectively;
   and further forming said heel portion to assume a curved shape.

4. The method of healing or preventing decubitus on the heel of a bedfast patient, comprising,
   forming an L-shaped member having a leg portion, a heel portion on one end of said leg portion, and a foot portion extending from said heel portion at right angles to said leg portion; and further forming said heel portion to have an interior surface whereby said interior surface is open to direct visual access from a lateral direction with respect to said L-shaped member,
   placing said L-shaped member on the leg and foot of a patient so that said leg and foot of said patient are in intimate contact with said leg portion and said foot portion, respectively, and so that the heel of said patient is spaced from said heel portion to prevent the application of pressure to the patient's heel by said heel portion.

5. The method of claim 4 including the further step of securing said L-shaped member to the leg and foot of said patient by using a sandal extending substantially over said foot portion and the foot of the patient, and cutting out a heel portion of said sandal adjacent said heel portion of said L-shaped member and said space.

6. The method of claim 4 wherein said L-shaped member is formed so that said leg, heel and foot portions are integral with each other.

* * * * *

UNITED STATES PATENT AND TRADEMARK OFFICE
CERTIFICATE OF CORRECTION

PATENT NO. : 5,298,013
DATED : March 29, 1994
INVENTOR(S) : Robert Lonardo

It is certified that error appears in the above-indentified patent and that said Letters Patent is hereby corrected as shown below:

On the title page, change the [*] Notice to read as follows:

--[*] Notice: The portion of the term of this patent subsequent to October 14, 1995, has been disclaimed. --.

Signed and Sealed this

Thirteenth Day of December, 1994

Attest:

BRUCE LEHMAN

*Attesting Officer*  *Commissioner of Patents and Trademarks*

REEXAMINATION CERTIFICATE (3568th)

United States Patent [19]

Lonardo

[11] B1 5,298,013

[45] Certificate Issued  *Jul. 7, 1998

[54] METHOD OF HEALING THE DECUBITUS ON THE HEEL OF A BEDFAST PATIENT

[75] Inventor: Robert Lonardo, Treasure Island, Fla.

[73] Assignee: Restorative Care of America Incorporated, Clearwater, Fla.

Reexamination Request:
No. 90/003,494, Jul. 11, 1994

Reexamination Certificate for:
Patent No.: 5,298,013
Issued: Mar. 29, 1994
Appl. No.: 52,517
Filed: Apr. 29, 1993

[*] Notice: The portion of the term of this patent subsequent to Dec. 14, 2010, has been disclaimed.

Related U.S. Application Data

[62] Division of Ser. No. 2,022, Feb. 16, 1993, Pat. No. 5,269,748, which is a continuation of Ser. No. 399,365, Sep. 21, 1973, abandoned, which is a continuation-in-part of Ser. No. 237,643, Mar. 24, 1972, abandoned, which is a continuation-in-part of Ser. No. 86,647, Nov. 4, 1970, abandoned.

[51] Int. Cl.$^6$ ........................................ A61F 5/00
[52] U.S. Cl. ........................ 602/28; 602/27; 128/882
[58] Field of Search ........................ 602/5, 23, 27–29; 128/845, 882

[56] References Cited

U.S. PATENT DOCUMENTS

| | | |
|---|---|---|
| 33,762 | 12/1861 | Lonardo . |
| 1,332,047 | 2/1920 | Lasher . |
| 2,847,991 | 8/1958 | Andrews . |
| 3,527,209 | 9/1970 | Baker . |
| 3,606,884 | 9/1971 | Peter . |
| 3,976,059 | 8/1976 | Lonardo . |

OTHER PUBLICATIONS

1921 Feick Brothers Co. Surgical Insrument Catalog, Tab "3".
1955 Zimmer Fracture Equipment Catalog, Tab "4".
1929 The Schuemann–Jones Co. Hosp. Supplies Catalog, Tab "3".
Jun. 1967 Providence Sunday Journal Business Weekly, Tab "7".
DePuy Fracture Appliances.
Ponseti Lower Extremity Braces.
1967 Newspaper Article.

*Primary Examiner*—Linda C. M. Dvorak

[57] ABSTRACT

A therapeutic leg and foot device comprising an L-shaped member having an elongated channel-like portion adapted to fit the posterior region of the lower leg and a foot portion extending integrally at right angles therefrom. The integral connection is curved to avoid contact with the patient's heel when the device is in place. The channel shape flattens out at the curved portion and is narrowed to promote the required flexing at this point. The device is constructed of resilient transparent acrylic plastic material which is resilient under a stress load but has sufficient rigidity to maintain a bed patient's foot in properly disposed position to prevent bed sores or drop foot. However, when used in the correction of drop foot, the foot portion is flexed away from perpendicular to an obtuse angle with the leg portion to conform to the deformity. In this position, the device exerts a 30 to 50 lb. pressure on the foot area to bias the foot back into normal position. There is also an equal amount of pressure or counter force on the lateral arch to correct outward turning of a foot usually associated with a foot drop deformity. This rigid flexibility also permits its use as an ambulation aid in gait training. The device is provided with releasable means for securing to the patient's foot. Attachments may be made for preventing undesirable rotation of the leg; for making the device rigid to maintain the immobility of the foot and heel; and for maintaining the bed sheets and blankets in spaced relation to the patient's toes.

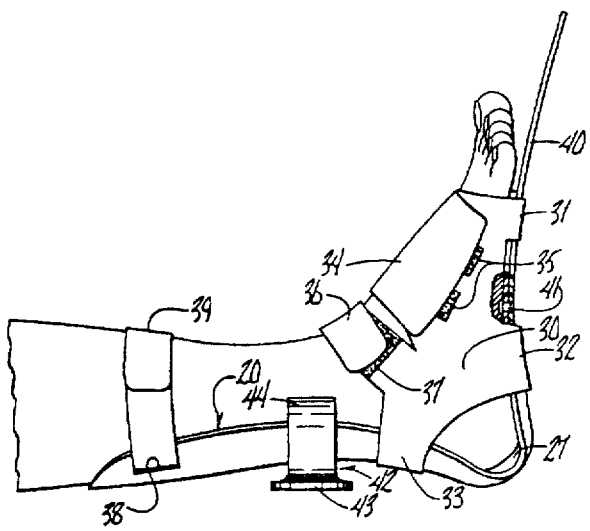

REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

Claims 1–6 are cancelled.

* * * * *